(12) United States Patent
Bottomley et al.

(10) Patent No.: US 9,791,489 B2
(45) Date of Patent: Oct. 17, 2017

(54) HIGH DYNAMIC RANGE RF POWER MONITOR

(75) Inventors: Paul A. Bottomley, Baltimore, MD (US); William Edelstein, Baltimore, MD (US); Abdel-Monem M. El-Sharkawy, Baltimore, MD (US); Di Qian, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 282 days.

(21) Appl. No.: 14/005,804

(22) PCT Filed: Mar. 22, 2012

(86) PCT No.: PCT/US2012/030173
§ 371 (c)(1),
(2), (4) Date: Sep. 17, 2013

(87) PCT Pub. No.: WO2012/129430
PCT Pub. Date: Sep. 27, 2012

(65) Prior Publication Data
US 2014/0015547 A1    Jan. 16, 2014

Related U.S. Application Data

(60) Provisional application No. 61/466,194, filed on Mar. 22, 2011.

(51) Int. Cl.
| | |
|---|---|
| *G01R 27/32* | (2006.01) |
| *G01R 21/00* | (2006.01) |
(Continued)

(52) U.S. Cl.
CPC ............ *G01R 27/32* (2013.01); *G01R 21/00* (2013.01); *G01R 33/3614* (2013.01); *A61N 1/00* (2013.01);
(Continued)

(58) Field of Classification Search
CPC ....... A61B 1/00; A61B 17/00; A61B 2217/00; G01R 1/00; G06F 1/00; G06F 2101/00; A61N 1/00
See application file for complete search history.

(56) References Cited

U.S. PATENT DOCUMENTS 5,128,629 A * 7/1992 Trinh .......................... 330/129
5,214,372 A * 5/1993 Vaisanen ................ G01R 21/01
324/114
(Continued)

FOREIGN PATENT DOCUMENTS

| | | |
|---|---|---|
| JP | H08-191816 A | 7/1996 |
| JP | 2001-095773 A | 4/2001 |
| KR | 10-2008-0027135 | 3/2008 |

OTHER PUBLICATIONS

An et al., Spectral localization by imaging using multielement receiver coils, Magnetic Resonance in Medicine, (2011).
(Continued)

*Primary Examiner* — Huy Q Phan
*Assistant Examiner* — Temilade Rhodes-Vivour
(74) *Attorney, Agent, or Firm* — Venable LLP; Henry J. Daley; Laura G. Remus

(57) ABSTRACT

A device with at least one channel for measuring high dynamic range, radio frequency (RF) power levels over broad-ranging duty cycles includes a power sensor circuit comprising at least one logarithmic amplifier; at least one directional RF coupler electrically connected to the at least one power sensor; at least one RF attenuator electrically connected to the at least one RF coupler; and at least one sampling circuit electrically connected to the at least one RF attenuator and the at least one RF coupler. The at least one sampling circuit performs analog-to-digital conversion of
(Continued)

electrical signals received to provide digitals signals for measuring the RF power level in the at least one channel.

17 Claims, 8 Drawing Sheets

(51) Int. Cl.
```
G01R 33/36    (2006.01)
A61N 1/00     (2006.01)
G06F 1/00     (2006.01)
G01R 1/00     (2006.01)
G01R 21/10    (2006.01)
G01R 33/28    (2006.01)
```

(52) U.S. Cl.
CPC ............ *G01R 1/00* (2013.01); *G01R 21/10* (2013.01); *G01R 33/288* (2013.01); *G06F 1/00* (2013.01); *G06F 2101/00* (2013.01)

(56) References Cited

U.S. PATENT DOCUMENTS

| | | | |
|---|---|---|---|
| 5,903,149 A | 5/1999 | Gonen et al. | |
| 5,982,165 A * | 11/1999 | Bowyer | G01R 19/0007 324/509 |
| 6,310,646 B1 * | 10/2001 | Shi | H04N 17/00 324/95 |
| 6,426,623 B1 | 7/2002 | Bernstein | |
| 6,521,874 B2 * | 2/2003 | Thompson | H02M 7/48 219/663 |
| 7,098,646 B2 | 8/2006 | Rose | |
| 7,652,464 B2 * | 1/2010 | Lang | H03G 1/00 324/95 |
| 7,822,565 B2 | 10/2010 | Brouk et al. | |
| 2003/0151453 A1 * | 8/2003 | Laletin | H03K 5/06 327/551 |
| 2004/0100325 A1 * | 5/2004 | van Amerom | H03G 3/3042 330/144 |
| 2005/0130595 A1 * | 6/2005 | Shurvinton | H03G 3/3047 455/67.11 |
| 2005/0227625 A1 * | 10/2005 | Diener | 455/67.7 |
| 2007/0242715 A1 * | 10/2007 | Gustavsson | H01S 5/18355 372/45.01 |
| 2007/0249928 A1 | 10/2007 | Blezek et al. | |
| 2008/0177163 A1 * | 7/2008 | Wang et al. | 600/324 |
| 2008/0280583 A1 * | 11/2008 | Chattopadhyay et al. | 455/327 |
| 2009/0251926 A1 * | 10/2009 | Choi | H02M 3/33569 363/16 |
| 2011/0066025 A1 | 3/2011 | Bahn | |
| 2011/0148411 A1 | 6/2011 | Bottomley et al. | |
| 2011/0152673 A1 * | 6/2011 | Doerr | A61N 1/3718 600/421 |
| 2014/0015529 A1 | 1/2014 | Bottomley et al. | |

OTHER PUBLICATIONS

Hu et al., SLIM: spectral localization by imaging, Magnetic Resonance in Medicine, 8 (1988) 314-322.
Liang et al., Constrained reconstruction methods in MR imaging, Rev Magn Reson Med, 4 (1992) 67-185.
Liang et al., A generalized series approach to MR spectrocopic imaging, IEEE Transactions Medical Imaging, 10 (1991) 132-137.
Von Kienlin et al., Spectral localization with optimal pointspread function, Journal of Magnetic Resonance, 94 (1991) 268-287.
Zhang et al., "Magnetic resonance Spectroscopy with Linear Algebraic Modeling (SLAM) for higher speed and sensitivity," Journal of Magnetic Resonance, 2012, vol. 218, pp. 66-76.
Akoka et al., "Radiofrequency map of an NMR coil by imaging," Magn Reson Imaging 11, 437-441 (1993).
Baker et al., "Evaluation of specific absorption rate as a dosimeter of MRI-related implant heating," J Magn Reson Imaging 20, 315-320 (2004).
Bottomley et al., "RF magnetic field penetration, phase-shift and power dissipation in biological tissue: implications for NMR Imaging," Physics in Medicine and Biology 23, 630-643 (1978).
Bottomley et al., "Homogeneous tissue model estimates of RF power deposition in human NMR studies—local elevations predicted in surface coil decoupling," Ann. N.Y. Acad. Sci. 649, 144-159 (1992).
Bottomley et al., "Power deposition in whole-body NMR imaging," Med Phys 8, 510-512 (1981).
Bottomley, "Turning up the heat on MRI," Journal of the American College of Radiology 5, 853-855 (2008).
Bottomley et al., "Designing passive MRI-safe implantable conducting leads with electrodes," Med Phys 37, 3828-3843 (2010).
Bottomley et al., "Estimating radiofrequency power deposition in body NMR imaging," Magn Reson Med 2, 336-349 (1985).
Brix et al., "Sampling and evaluation of specific absorption rates during patient examinations performed on 1.5-Tesla MR systems," Magn Reson Imaging 19, 769-779 (2001).
Collins et al., "Calculation of radiofrequency electromagnetic fields and their effects in MRI of human subjects," Magn Reson Med 65, 1470-1482 (2011).
Collins et al., "SAR and Bi field distributions in a heterogeneous human head model within a birdcage coil. Specific energy absorption rate," Magn Reson Med 40, 847-856 (1998).
Collins et al., "Temperature and SAR calculations for a human head within volume and surface coils at 64 and 300 MHz," J Magn Reson Imaging 19, 650-656 (2004).
Edelstein et al., "Electronic method for eliminating prescanning RF transmitter amplitude adjustment", Society of Magnetic Resonance in Medicine Sixth Annual Meeting, p. 372. New York, NY, USA, (1987).
Edelstein et al., "The intrinsic signal-to-noise ratio in NMR imaging," Magn Reson Med 3, 604-618 (1986).
Ehses et al., "MRI thermometry: Fast mapping of RF-induced heating along conductive wires," Magn Reson Med 60, 457-461 (2008).
El-Sharkawy et al., "The performance of interventional loopless MRI antennae at higher magnetic field strengths," Med Phys 35, 1995-2006 (2008).
El-Sharkawy et al., "A Multi-Channel, High Dynamic Range, Real Time RF Power Deposition Monitor", Proc Int Soc Magn Reson Med p. 496. Montreal, Canada, (2011).
El-Sharkawy et al., "Accurate Measurement of RF Power Deposition During 3T MRI", 18th Annual Meeting, Int Soc Magn Reson Med p. 3853. Stockholm, Sweden, (2010).
Guidance for Industry and FDA: "Staff Criteria for Significant Risk Investigations of Magnetic Resonance Diagnostic Devices, "United States Food and Drug Administration (FDA), 2003.
Homann et al., "Toward individualized SAR models and in vivo validation," Magn Reson Med 66, 1767-1776 (2011).
Ibrahim et al., "Analysis of B 1 field profiles and SAR values for multi-strut transverse electromagnetic RF coils in high field MRI applications," Physics in Medicine and Biology 46, 2545-2555 (2001).
Ibrahim et al., "Dielectric resonances and B(1) field inhomogeneity in UHFMRI: computational analysis and experimental findings," Magn Reson Imaging 19, 219-226 (2001).
Kumar et al., "Noise figure limits for circular loop MR coils," Magn Reson Med 61, 1201-1209 (2009).
Liu et al., "Calculations of B-1 distribution, specific energy absorption rate, and intrinsic signal-to-noise ratio for a body-size birdcage coil loaded with different human subjects at 64 and 128 MHz," Appl. Magn. Reson. 29, 5-18 (2005).
Mattei et al., "MRI induced heating of pacemaker leads: effect of temperature probe positioning and pacemaker placement on lead tip heating and local SAR," Conf Proc IEEE Eng Med Biol Soc 1, 1889-1892 (2006).
Muranaka et al., "Dependence of RF heating on SAR and implant position in a 1.5T MR system," Magn Reson Med Sci 6, 199-209 (2007).
Nguyen et al., "Numerical evaluation of heating of the human head due to magnetic resonance imaging," IEEE Trans Biomed Eng 51, 1301-1309 (2004).

(56) References Cited

OTHER PUBLICATIONS

Nitz et al., "Specific absorption rate as a poor indicator of magnetic resonance-related implant heating," Invest Radiol 40, 713776 (2005).
Oh et al., "Experimental and numerical assessment of MRI-induced temperature change and SAR distributions in phantoms and in vivo," Magn Reson Med 63, 218-223 (2010).
Schar et al., "Simultaneous B(o)- and B(1)+-map acquisition for fast localized shim, frequency, and RF power determination in the heart at 3 T," Magn Reson Med 63, 419-426 (2010).
Shellock, "Comments on MR heating tests of critical implants," J Magn Reson Imaging 26, 1182-1185 (2007).
Simunic, "Calculation of energy absorption in a human body model in a homogeneous pulsed high-frequency field," Bioelectrochem. Bioenerg. 47, 221230 (1998).
Stralka et al., "A prototype RF dosimeter for independent measurement of the average specific absorption rate (SAR) during MRI," J Magn Reson Imaging 26, 1296-1302 (2007).
Wang et al., "Theoretical and experimental investigation of the relationship among SAR, tissues and radio frequencies in MRI," Physica Medica 21, 61-64 (2005).
Wang et al., "SAR and temperature: simulations and comparison to regulatory limits for MRI," J Magn Reson Imaging 26, 437-441 (2007).
Weber et al., "A ultra high field multi-element transceive volume array for small animal MRI," Conf Proc IEEE Eng Med Biol Soc 2008, 2039-2042 (2008).
Zaremba, "FDA Guidelines for Magnetic Resonance Equipment Safety", The American Association of Physicists in Medicine Annual Meeting, p. 8356. Palais des Congres de Montreal, (2002).
International Search Report and Written Opinion of PCT/2012/030173.
International Search Report and Written Opinion of PCT/US2012/030176.
Bashir et al., Natural linewidth chemical shift imaging (NLqCSI), Magnetic Resonance in Medicine, 56 (2006) 7-18.
Basser et al., MR diffusion tensor spectroscopy and imaging. Biophys J 1994;66(1):259.
Beer et al., Absolute concentrations of high-energy phosphate metabolites in normal, hypertrophied, and failing human myocardium measured noninvasively with 31P-SLOOP magnetic resonance spectroscopy, J Am Coll Cardiol, 40 (2002) 1267-1274.
Biswal et al., Functional connectivity in the motor cortex of resting human brain using echo-planar mri. Magn Reson Med 1995;34(4):537-541.
Borthakur et al., Sodium and T1p MRI for molecular and diagnostic imaging of articular cartilage. NMR Biomed 2006;19(7):781-821.
Bottomley et al., A review of normal tissue hydrogen NMR relaxation times and relaxation mechanisms from 1-100 MHz: dependence on tissue type, NMR frequency, temperature, species, excision, and age. Med Phys 1984;11:425.
Bottomley et al., Four-angle saturation transfer (FAST) method for measuring creatine kinase reaction rates in vivo. Magn Reson Med 2002;47(5):850-863.
Bottomley et al., Problems and expediencies in human 31P spectroscopy. The definition of localized volumes, dealing with saturation and the technique-dependence of quantification, NMR in Biomedicine, 2 (1989) 284-289.
Bottomley et al., Strategies and Protocols for Clinical 31P Research in the Heart and Brain, Phil. Trans. R. Soc. Lond. A, 333 (1990) 531-544.
Bottomley, NMR Spectroscopy of the Human Heart, in: R.K. Harris, R.E. Wasylishen (Eds.) Encyclopedia of Magnetic Resonance, John Wiley: Chichester, 2009.
Bottomley, Spatial localization in NMR spectroscopy in vivo, Annal NY Acad Sci, 508 (1987) 333-348.
Brooker et al., Selective Fourier transform localization, Magnetic Resonance in Medicine, 5 (1987) 417-433.
Brown et al., NMR chemical shift imaging in three dimensions, Proc. Natl Acad Sci USA, 79 (1982) 3523-3526.
Chavhan et al., Principles, Techniques, and Applications of T2*-based MR Imaging and Its Special Applications 1. Radiographics 2009;29(5):1433-1449.
Conway et al., Mitral regurgitation: Impaired systolic function, eccentric hypertrophy, and increased severity are linked to lower phosphocreatine/ATP ratios in humans, Circulation, 97 (1998) 1716-1723.
Detre et al., Perfusion imaging. Magn Reson Med 1992;23(1):37-45.
Dong et al., Lipid signal extraction by SLIM: Application to 1H MR spectroscopic imaging of human calf muscles, Magnetic Resonance in Medicine, 55 (2006) 1447-1453.
Ei-Sharkawy et al., Quantitative cardiac 31P spectroscopy at 3 Tesla using adiabatic pulses, Magnetic Resonance in Medicine, 61 (2009) 785-795.
Forsén et al., Study of moderately rapid chemical exchange reactions by means of nuclear magnetic double resonance. The Journal of Chemical Physics 1963;39(11):2892-2901.
Frahm et al., Localized high-resolution proton NMR spectroscopy using stimulated echoes: Initial applications to human brain in vivo, Magnetic Resonance in Medicine, 9 (1989) 79-93.
Gabr et al., Quantifying in vivo MR spectra with circles, Journal of Magnetic Resonance, 179 (2006) 152-163.
Hoge et al., A tour of accelerated parallel MR imaging from a linear systems perspective. Concepts Magn Reson Part A 2005;27(1):17-37.
Jacob et al., Improved model-based magnetic resonance spectroscopic imaging, Medical Imaging, IEEE Transactions on, 26 (2007) 1305-1318.
Khalidov et al., BSLIM: Spectral Localization by Imaging With Explicit BO Field Inhomogeneity Compensation, Medical Imaging, IEEE Transactions on, 26 (2007) 990-1000.
Kim et al., Water saturation shift referencing (WASSR) for chemical exchange saturation transfer (CEST) experiments. Magn Reson Med 2009;61(6):1441-1450.
Kmiecik et al., Lactate quantitation in a gerbil brain stroke model by GSLIM of multiple-quantum-filtered signals, J Magn Reson Imaging, 9 (1999) 539-543.
Loan CFV. The ubiquitous Kronecker product. J Comput Appl Math 2000;123(1):85-100.
Loffler et al., Localized spectroscopy from anatomically matched compartments: improved sensitivity and localization for cardiac 31P MRS in humans, Journal of Magnetic Resonance, 134 (1998) 287-299.
Meininger et al., Concentrations of human cardiac phosphorus metabolites determined by SLOOP 31P NMR spectroscopy, Magnetic Resonance in Medicine, 41 (1999) 657-663.
Ordidge, A. Connelly, J. Lohman, Image-selected in vivo spectroscopy (ISIS). A new technique for spatially selective NMR spectroscopy, Journal of Magnetic Resonance (1969), 66 (1986) 283-294.
Panych et al., PSFqchoice: A novel MRI method for shaping point spread functions in phase encoding dimensions, Magnetic Resonance in Medicine, 54 (2005) 159-168.
Posse et al., MR spectroscopic imaging: principles and recent advances. J Magn Reson Imaging 2013;37(6):1301-1325.
Pruessmann et al., Advances in sensitivity encoding with arbitrary k-space trajectories. Magn Reson Med 2001;46(4):638-651.
Pruessmann et al., SENSE: sensitivity encoding for fast MRI. Magn Reson Med 1999;42(5):952-962.
Schär et al., Triple repetition time saturation transfer (TRiST) 31P spectroscopy for measuring human creatine kinase reaction kinetics. Magn Reson Med 2010;63(6):1493-1501.
Smith et al., Altered Creatine Kinase Adenosine Triphosphate Kinetics in Failing Hypertrophied Human Myocardium, Circulation, 114 (2006) 1151-1158.
Von Kienlin et al., Advances in human cardiac 31P-MR spectroscopy: SLOOP and clinical applications, J Magn Reson Imaging, 13 (2001) 521-527.
Ward et al., A new class of contrast agents for MRI based on proton chemical exchange dependent saturation transfer (CEST). J Magn Reson 2000;143(1):79-87.

(56) References Cited

OTHER PUBLICATIONS

Weiss et al., ATP flux through creatine kinase in the normal, stressed, and failing human heart, Proc Natl Acad Sci USA, 102 (2005) 808-813.

Weiss et al., Regional Myocardial Metabolism of High-Energy Phosphates during Isometric Exercise in Patients with Coronary Artery Disease, N Engl J Med, 323 (1990) 1593-1600.

Wolff et al., Magnetization transfer contrast (MTC) and tissue water proton relaxation in vivo. Magn Reson Med 1989;10(1):135-144.

Zhang et al., Dramatic speedup in 1 D-, 2D- and 3D- MRS scan times with linear algebraic modeling (SLAM), in: Proceedings of the International Society for Magnetic Resonance in Medicine, in press, 2012.

Zhang et al., Highly-accelerated quantitative 2D and 3D localized spectroscopy with linear algebraic modeling (SLAM) and sensitivity encoding. J Magn Reson 2013;237:125-138.

Zhou et al., Practical data acquisition method for human brain tumor amide proton transfer (APT) imaging. Magn Reson Med 2008;60(4):842-849.

Zhou et al., Three-dimensional amide proton transfer MR imaging of gliomas: Initial experience and comparison with gadolinium enhancement. J Magn Reson Imaging 2013;38(5):1119-1128.

\* cited by examiner

HIGH DYNAMIC RANGE RF POWER MONITOR

CROSS-REFERENCE OF RELATED APPLICATION

This is a national stage application under 35 U.S.C. §371 of PCT/US2012/030173 filed Mar. 22, 2012, the entire contents of which are incorporated herein by reference and this application claims priority to U.S. Provisional Application No. 61/466,194 filed Mar. 22, 2011, the entire contents of which are hereby incorporated by reference.

This invention was made with government support under R01EB007829 awarded by the National Institutes of Health. The government has certain rights in the invention.

BACKGROUND

1. Field of Invention

The field of the currently claimed embodiments of this invention relates to high dynamic range (DR) radio frequency (RF) power monitoring devices and methods.

2. Discussion of Related Art

Accurate knowledge of the RF specific absorption rate (SAR) in the body during magnetic resonance imaging (MRI) scans is important for patient safety and compliance with limits mandated by the Food and Drug Administration (FDA) in the USA[1] and the International Electro-technical Commission (IEC) in Europe.[2] In addition to ensuring safe operation and regulatory compliance, accurate power monitoring can avoid restrictions on clinical MRI sequences arising from incorrect estimation of the delivered power. Accurate knowledge of delivered power is essential for testing the MRI safety of peripheral, implanted and interventional devices at defined RF exposure levels.[3-6]

RF safety concerns initially arose with the introduction of higher-field 1.5 Tesla (T) whole-body MRI scanners and the recognition that SAR increases approximately with the square of MRI frequency or field-strength when other MRI sequence parameters are kept constant.[7-9] The recent emergence of clinical 3 T scanners and experimental body systems operating at 7 T and higher,[10] in which SAR could potentially increase 4- to more than 20-fold compared to 1.5 T, only exacerbates concerns about safety and how to ensure compliance with SAR guidelines.[1,2]

In clinical MRI scanners, SAR monitoring for safety and regulatory compliance is generally carried out by scanner software and hardware that is largely proprietary, with "scanner SAR" values typically logged for each study. These systems prohibit or terminate scanning based on predictions of body SAR relying on internal measures, modeling, and prior characterization or assumed properties of the MRI transmit coil. Electromagnetic modeling with knowledge of the input power [11-13] and thermal mapping[14,15] can help provide a detailed understanding of whole body and local SAR. Yet, rare as they may be compared to the total number of MRI scans performed, RF burns do occur, a fraction of which are reported to the FDA.[16] In these cases, at least, a failure in scanner SAR monitoring has occurred.

Unfortunately, investigating whether the scanner is operating safely within SAR guidelines by means that are independent of the scanner, if performed at all, is not easy.[17] The accuracy of scanner SAR estimates is also questionable in light of discrepancies with thermally-derived SAR measurements,[17,18] especially during MRI safety-testing of interventional devices[3, 18-20] and the lack of correlation between subjective heat perception by patients and scanner SAR.[21]

Setting precise SAR exposure levels for investigators testing devices or MRI methods, or for evaluating SAR in individual burn cases,[22] requires accurate and independent measurement tools. This starts with accurate measurements of the total power deposited and requires a reliable RF power meter. The RF power monitors built into the MRI scanner are usually attached to the RF power amplifier output. However, measuring the power delivered to the body is complicated by losses in the RF transmission chain, including the cables, switches, the quadrature-hybrid (Q-hybrid) and the MRI coil.[23,24] These losses can vary over time, but are not routinely monitored.

Moreover, as we now report, the very high dynamic range (typically >20 dB) (DR=peak-to-average power ratio) of RF transmit pulses, and MRI duty cycles that span orders-of-magnitude, are beyond the capabilities of available commercial power meters.[25] These meters are adequate for pulse sequences with short repetition periods (TR) and consistent high power levels. However, they do not give accurate results for sequences using mixtures of high and low amplitudes or modulations, or long TR. There thus remains a need for improved systems and methods for measuring high dynamic range, low duty cycle (typically <1%) RF power.

SUMMARY

A device with at least one channel for measuring high dynamic range, radio frequency (RF) power levels over broad-ranging duty cycles according to an embodiment of the current invention includes a power sensor circuit comprising at least one logarithmic amplifier; at least one directional RF coupler electrically connected to the at least one power sensor; at least one RF attenuator electrically connected to the at least one RF coupler; and at least one sampling circuit electrically connected to the at least one RF attenuator and the at least one RF coupler. The at least one sampling circuit performs analog-to-digital conversion of electrical signals received to provide digitals signals for measuring the RF power level in the at least one channel.

A method of monitoring RF exposure proximate an RF emitting device according to an embodiment of the current invention includes connecting an RF monitoring system according to an embodiment of the current invention to an RF power source of said RF emitting device.

BRIEF DESCRIPTION OF THE DRAWINGS

Further objectives and advantages will become apparent from a consideration of the description, drawings, and examples.

FIG. 6A shows scanner B1 linear pulse envelope simulator. FIG. 6B shows recorded time window of RF power in real time for long RF pulses. FIG. 6C shows a single pulse (logarithmic scale).

FIG. 7A shows Philips Medical System's 3 Tesla (T) Achieva amplifier output power measurements using the PPMM (solid circles), and the scanner power monitoring unit (open diamonds, reported in the log file), vs. scanner average predicted power. Power data are from 11 human volunteers, plus four measurements from mineral oil bottles (circled), using short (1 ms) and long (7 ms) slice-selective pulses. The line represents identity. FIG. 7B shows total power deposited in the body measured by the PPMM, as a function of BMI. Lines of best fit correspond to long and short pulses. Also shown is the PPMM-measured whole-body SAR for (FIG. 7C) short and (FIG. 7D) long pulses, as compared to the scanner predicted SAR from scanner log files (horizontal lines).

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Some embodiments of the current invention provide a high-DR, MRI-compatible, power profiling system for measuring and recording RF power over a wide range of MRI scan conditions. The system is broadband up to 400 MHz, can be used to sample power for both local and whole-body power flow and, unlike commercial meters, has six channels and a buffer size suitable for monitoring power at multiple locations over extended time periods. We provide some examples of its application to real-time RF power monitoring in human whole-body MRI studies of volunteers performed in commercial Philips Medical Systems' (Best, The Netherlands) and Siemens Medical Solutions' (Malvern, Pa.) 3 T MRI scanners. We show that the power deposited and the body-average SAR,[1,2] often vary considerably from the scanners' own estimates.

RF Power Measurement

Figure 1:
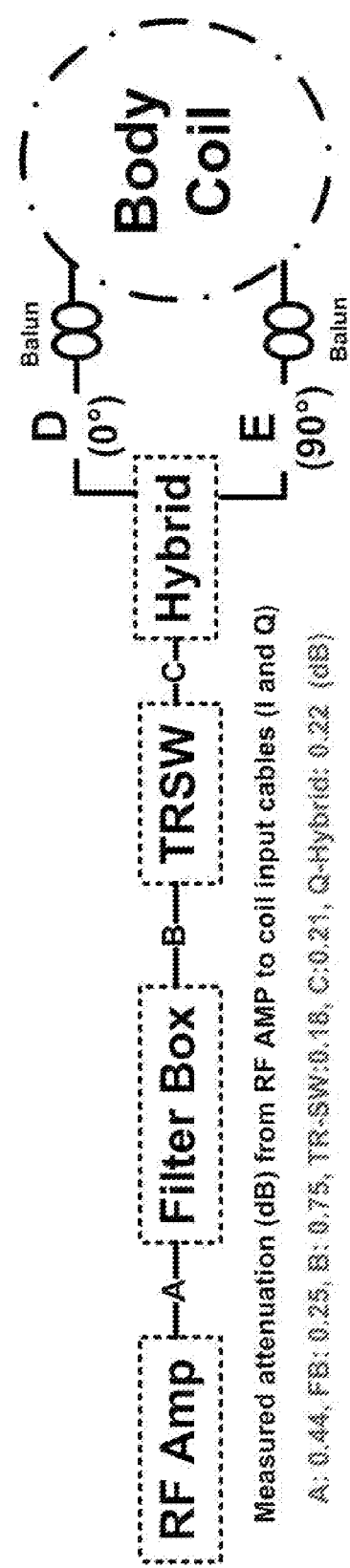
FIG. 1 is a schematic illustration of the Philips Achieva RF power delivery chain provided to facilitate a description of some embodiments of the current invention. Shown are the RF amplifier (RF AMP), measured cable attenuation factors (A, B, C), the filter box penetrating the scanner's Faraday cage, the transmit switch (TRSW) and the Q-hybrid.

In an example, the losses in the RF power chain of a Philips 3 T Achieva 3 T scanner[26] were first characterized using a 4395A Agilent Technologies (Santa Clara, Calif.) network analyzer by measuring the attenuation in each stage in accordance with the schematic in FIG. 1. Measured losses in these components show that the power output at the Q-hybrid (points D, E, FIG. 1) is only about 59% of the power out of the RF amplifier (point A). (See, for example, U.S. Pat. Pub. No. 2011/0148411; U.S. application Ser. No. 12/677,097 assigned to the same assignee as the current application, the entire content of which is incorporated herein by reference.)

To measure the pulse power during MRI, we first tried commercial inline power meters. Bird 5014 and Bird 5010b (Bird Technologies, Solon, Ohio) did not work correctly for peak/average power ratios greater than ten. Even when operating the scanner at minimum TRs and low RF field intensity ($B_1$), measurements were unstable and irreproducible.

We next used a Ladybug Technologies LLC (Santa Rosa, Calif.), LB480A power profiling meter in combination with 50 dB dual directional couplers to measure forward and reverse power at the outputs of the power amplifier and the Q-hybrid during MRI. The Ladybug meter sampled the pulse profile at 10 μs intervals and stored results for power calculations. While this yielded accurate measurements on four volunteers,[27] the use of USB cables from Ladybug to the computer necessitated a person inside the scanner room. Moreover, the Ladybug meter did not have sufficient channels for monitoring the forward and reverse power at the three locations of interest simultaneously (A, D, and E in FIG. 1, location A). In addition, its small buffer size (≤1 sec) was inadequate for providing continuous measurements of power for many MRI sequences with long TRs over the several cycles needed for accurately measuring time-averaged power, thus rendering real-time measurements impractical.

We therefore built a 6-channel scanner-independent power monitoring system according to an embodiment of the current invention. An embodiment has six power sensor circuits (PSC), (FIG. 2A) assembled from AD8310 logarithmic amplifier IC's (Analog Devices, Norwood Mass.). At each of three locations (RF amplifier output, two Q-hybrid outputs), a power profiling measurement module (PPMM) having a 50 dB directional coupler (Werlatone Inc., Patterson N.Y.) connected to two PSCs, one to its forward channel and one to its reverse channel (FIG. 2B), was deployed. A 10 dB attenuator was added to the forward channels to allow measurements of up to 50 kW of peak power. The design DR was from 17 dBm (nearly the maximum input power of the AD8310) to −80 dBm over the desired frequency range 1-440 MHz. Each PSC is powered by a rechargeable lithium ion, non-magnetic 4V battery (PowerStream, Orem Utah) and can operate continuously for at least 10 hours before recharging. The video bandwidth of the ICs was set to 112 KHz using a 470 PF capacitor (FIG. 2A).

Figure 2A:
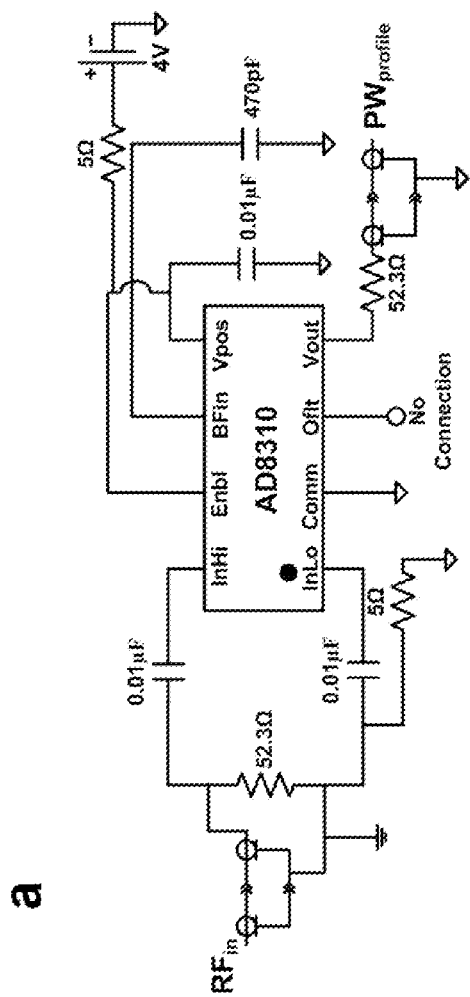
FIG. 2A provides a circuit diagram of a digital power sensor circuit (PSC) based on the AD8310 IC according to an embodiment of the current invention.
Figure 2B:
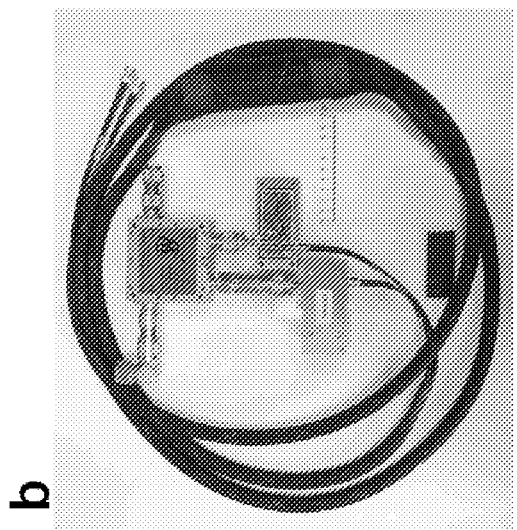
FIG. 2B shows an example of one of the three power profiling measurement modules (PPMM) showing the directional coupler and PSCs according to an embodiment of the current invention.

Although this embodiment describes three circuits, such as the one illustrated in the embodiment of FIGS. 2A and 2B, one, two, three or more such circuits could be used in various embodiments of the current invention.

Figure 3:
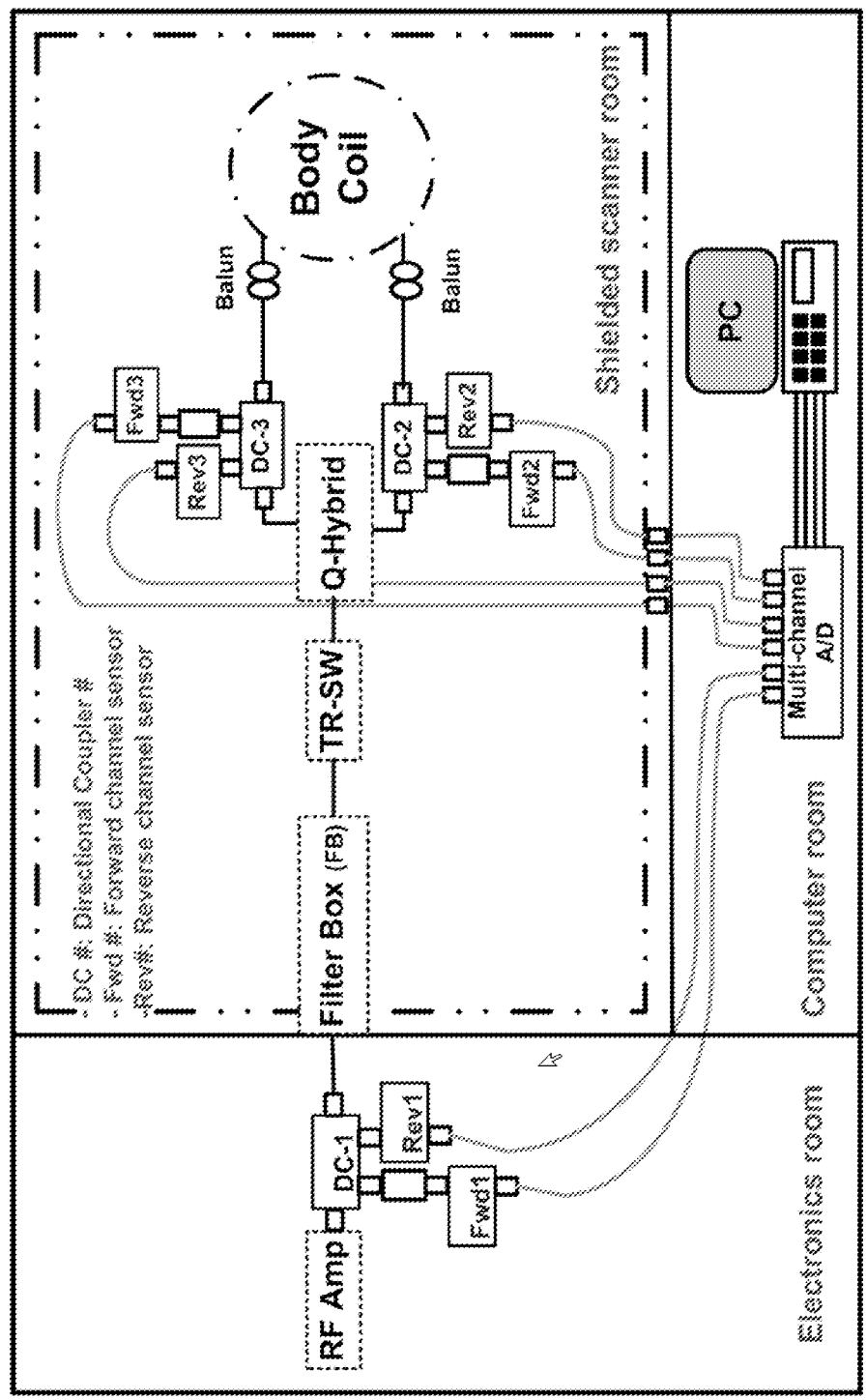
FIG. 3 is a schematic illustration of a device for measuring high dynamic range, low duty cycle radio frequency (RF) power levels according to an embodiment of the current invention.

The outputs of each of the six PSCs are simultaneously sampled in differential input mode at 200 kHz by a 16 bit USB-6251 National Instruments (Austin, Tex.) data acquisition system controlled by a laptop computer that also stores the power measurement data. The 5 μs sampling resolution accurately captures the MRI RF pulse modulation whose time resolution in the Philips scanner was about 6.4 μs. A MATLAB (The Mathworks, Natick, Mass.) program was written to read the saved voltage files, convert them to power profiles using the linear calibration curves for each channel, and to calculate average power values for all experiments. A schematic of the system configured to monitor RF power flow is shown in FIG. 3. The (low frequency) power profiling lines from the PPMMs attached to the quad hybrid outputs are fed through the scanner room's connection panel. The lines from the PPMM connected to the RF power amplifier were wound around ferrite cores to prevent RF interference.

Figures 4A, 4B, 4C:
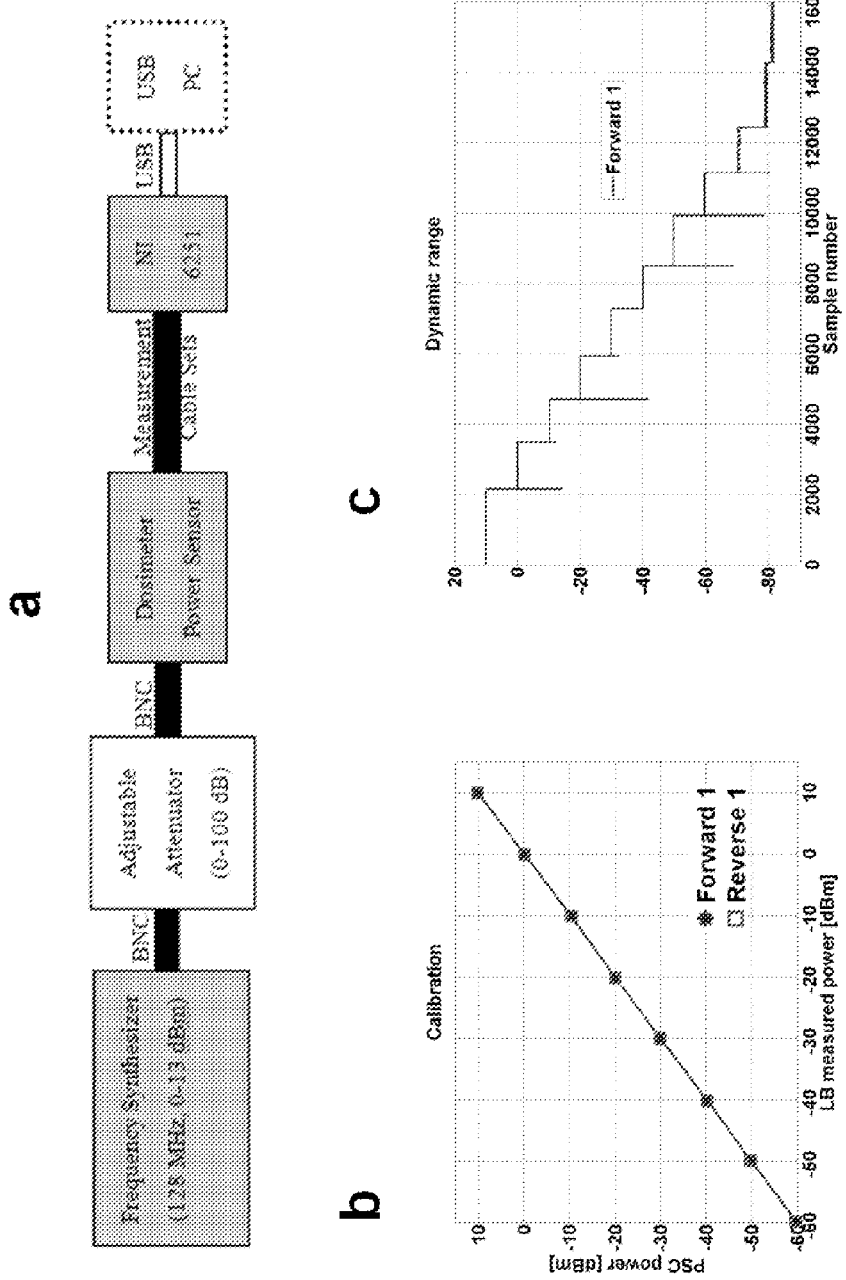
FIG. 4A is a schematic illustration of a bench setup for calibrating the Power Sensor Circuit (PSC) units as well as testing dynamic range and linear performance according to an embodiment of the current invention.
FIG. 4B shows a calibration curve, PSC vs. Ladybug meter showing linearity.
FIG. 4C shows PSC 90 dB dynamic range.

Each PPMM was bench calibrated for the operational frequencies of the Philips 3 T Achieva scanner and a Siemens 3 T Trio scanner (127.8 MHz and 123 MHz, respectively) using the setup shown in FIG. 4A. The calibration was performed against the LB480A meter using a 10 dBm frequency synthesizer whose output was connected to a 0-100 dB variable attenuator to vary the input power level. The PSC voltage-to-logarithmic power was measured over a 70 dB range (limited by the LB480A unit's operational dynamic range) and was highly linear as shown in FIG. 4. FIG. 4B. The slopes of the calibration curves were about 0.24 V/10 dBm. The net sampling resolution of the A/D was set to 0.004 dBm. After calibration the full DR was tested over a range of 90 dB as shown in FIG. 4C and exhibited a maximum deviation of 0.8 dBm from linearity at −80 dBm. The total insertion loss of the monitoring system PPMMs at 128 MHz was 0.1 dB or about 2%.

RF Power Deposition

Figure 5:
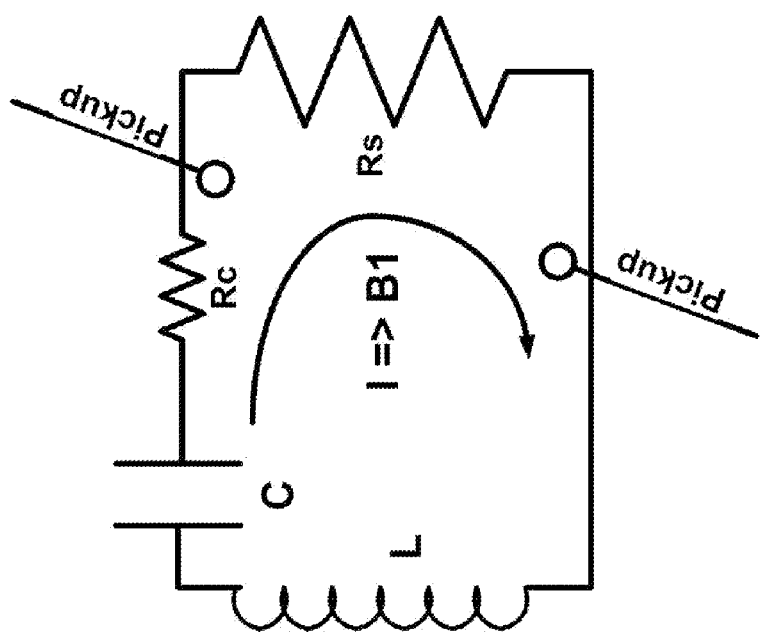
FIG. 5 is a schematic illustration of a resonant circuit for an MRI coil producing a certain transverse RF magnetic field, B1, to facilitate an explanation of some concepts of the current invention. Rc is the coil resistance and Rs is the resistance reflected into the coil circuit by the imaging subject load. B1 is proportional to current I in the coil and Power loss=$I^2 \cdot (Rc+Rs)$, where $R_c$ is the coil resistance and $R_s$ is the sample resistance at the RF, and I is the coil current. Shown also are pickup loops used by the scanner to monitor the B1 RF field produced by the coil.

FIG. 5 shows a schematic resonant circuit for an MRI coil producing a transmit RF field, B1, proportional to the current, I, in the coil. The power loss in the circuit is the sum of the coil and subject losses in resistive loads Rc and Rs, respectively. The pickup loops, are fixed by the manufacturer inside the RF body coil. They are used by the scanner to monitor and set the initial value of the RF field produced by the coil during set-up. The power loss in the coil $P_{coil}$, is measured as the net power flow at the output of the Q-hybrid with a lossless sample placed in the coil. The lossless sample is a 1 liter bottle of mineral oil whose RF dielectric constant, conductivity and size are orders-of-magnitude lower than those of the body.[28,29] This was verified by measuring $P_{coil}$ with additional mineral oil sample volumes of 2 liters and 3 liters; no significant change in power absorption was observed. The desired B1, and therefore the current I required to produce it, is approximately constant, independent of the subject being imaged.[30,31] Therefore the coil power dissipation, $P_{coil}$, is constant for a given pulse sequence, independent of the subject. The power deposited in the subject is then $P_{subject}=P_{total}-P_{coil}$, where $P_{total}$ is the total power dissipated in the coil plus the subject measured at the Q-hybrid. Note that larger subjects have greater $P_{total}$ but the same $P_{coil}$.

To measure the RF power deposited in human subjects during MRI, the power monitoring system was connected to the output of the RF power amplifier and the two outputs of the Q-hybrid before the scan. Eleven healthy volunteers (9 men, 2 women; age 22-65 yrs) were recruited and provided informed consent for this study approved by The Johns Hopkins Institutional Review Board on Human Investigation. Subjects were positioned in the Philips 3 T scanner and the scanner's automated scan preparation sequence initiated. Volunteers were landmarked at the xiphoid, placed at the isocenter of the scanner and a transverse slice containing both the heart and liver was targeted. A reference B1 RF field is first set based on pickup coil sensors, followed by the scanner's MRI-based B1 optimization algorithm which sets the final flip-angle. The B1 optimization algorithm is based on a stimulated echo sequence similar to the one described by Akoka et al.[32] where an average signal projection is used, thus rendering the result stable against local field variations. Two field-echo (FE) MRI sequences with TR=50 ms and two different RF pulse shapes (a short 1 ms asymmetric two lobe pulse and a long 7 ms "Spredrex" pulse[33]) were used.

The total scanner time per subject—including entry, positioning, and egress from the scanner—was 10-15 min.

The delivered RF power reported by the scanner, as well as the measured power output, was recorded. The subject was replaced by the mineral oil phantom and the pulse sequence repeated to produce the same B1 detected by the pickup coil. Scanner SAR and power were again recorded, along with the power measured by our power monitoring system. Body-average SAR was taken as the power deposited divided by the subject's weight, in accordance with the standard definition.[1,2]

The same protocol was repeated on six of the volunteers (men, age 23-66 yrs) in a Siemens 3 T Trio scanner. The FE sequence used the scanner's default 2 ms RF sinc pulse with one side lobe. The scanner's console SAR differed from the value reported in its log file, so both values were recorded.

All power values measured by our power monitoring system were calculated by averaging instantaneous power over a 0.5 s time window (10 pulses for FE pulse sequence).

Results

MRI experiments showed no noticeable interference or image degradation with the PPMMs connected. Connecting the PPMMs did not increase noise, as was confirmed by noise scans acquired with the RF and gradients turned off.

Figures 6A, 6B, 6C:
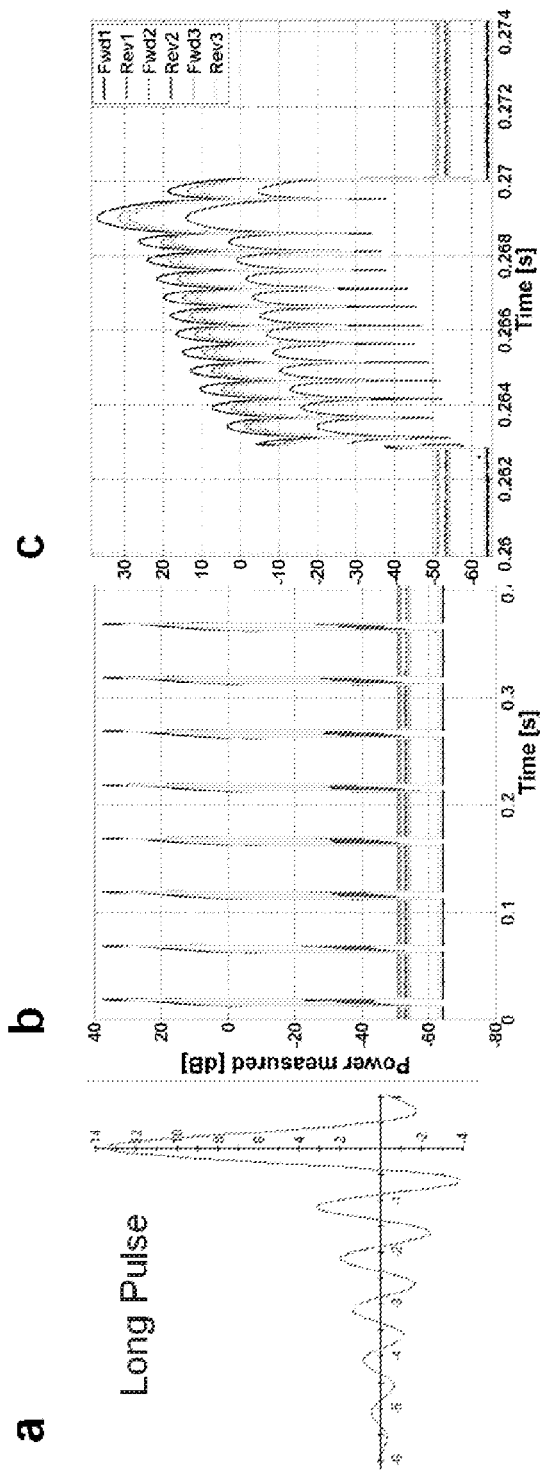
FIGS. 6A-6C show real-time profile of a ~7 ms asymmetric, slice selective RF pulse in the Philips scanner.

FIG. 6 exemplifies the 6-channel real-time recordings of an asymmetric, multi-lobe, slice selective RF pulse on the Philips scanner with a subject present. The detailed instantaneous recording of RF power is shown for Spredrex pulses on a logarithmic scale.[33]

Figures 7A, 7B, 7C, 7D:
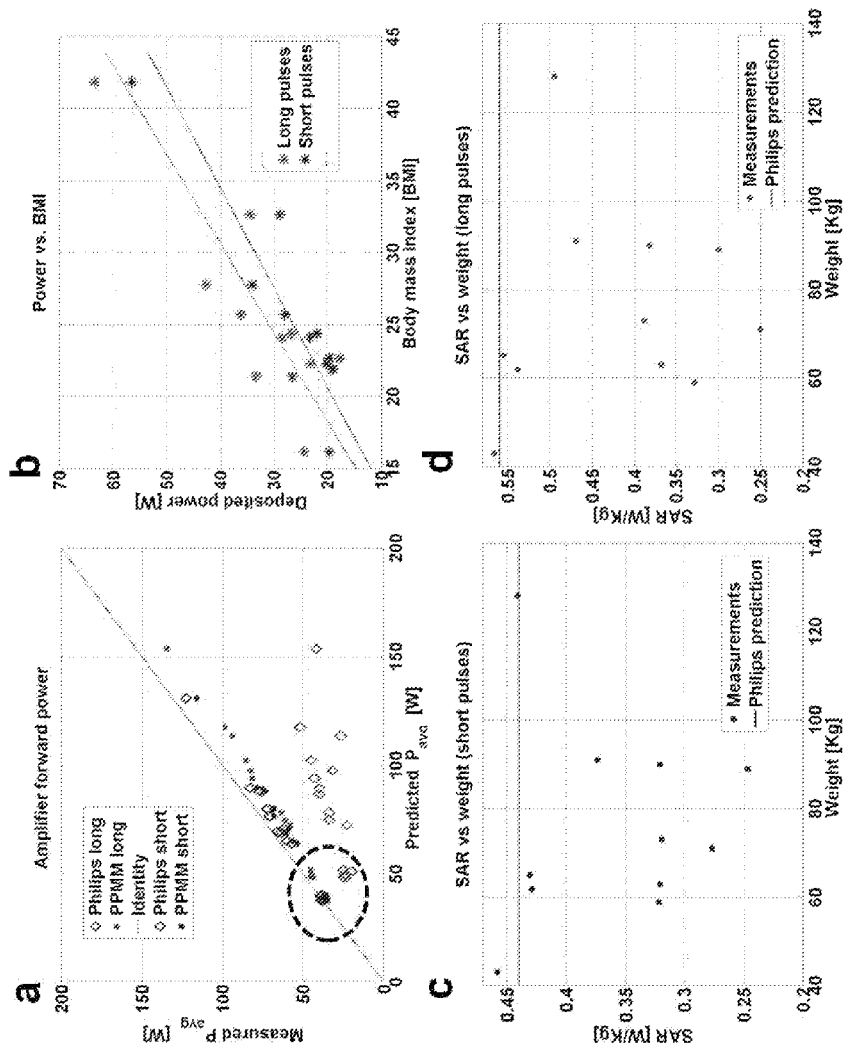
FIGS. 7A-7C show results for some measurements according to an embodiment of the current invention.

The results for the forward power delivered to the Philips body MRI coil and body average SAR for all subjects in the Philips scanner are plotted in FIG. 7 as a function of the power reported by the scanner, the patient weight, and the body mass index (BMI). FIG. 7A shows that the scanner-reported power at the RF amplifier's output agrees with our PPMM system results to within 6% for short pulses (~1 ms). This is not true for longer pulses (~7 ms), where the scanner's RF power monitoring fails when compared to the PPMM system that had been calibrated over the full DR and duty-cycles used for MRI. For all volunteers, the power delivered at the output of the Philips quadrature hybrid (Q-hybrid) is 56.5±2.5% of the output of the amplifier. This figure is consistent with the 58.5% predicted from the measured losses in the Philips RF chain plus the measured insertion losses in the power monitoring modules. For the 50 ms TR, the average power dissipated in the coil is 8.8±0.6 W for the short pulses and 11.1±0.8 W for the long pulses, independent of the size of the mineral oil bottle (1-3 liter).

The Philips Achieva scanner initially establishes a B1 that is the same for all samples using pickup loops. It is worth noting that the final MRI optimization yielded a B1 that was, on average, within 5% of the initial pickup loop B1 in all samples, from small to large human subjects as well as in the mineral oil bottles. This result supports the assumption that the current I required to produce a desired MRI flip angle across the slice projection is essentially independent of sample size, and that the power dissipation in the RF coil always equals the power dissipation with the mineral oil sample to a good approximation.

FIG. 7B shows that the measured deposited power varies linearly with BMI with a correlation coefficient $R^2=0.8$ (0.7) for short (long) RF pulses. FIG. 7C and FIG. 7D show that the scanner almost always overestimates body-average SAR. The scanner overestimated SAR by up to 78% for short pulses and 123% for long pulses when compared to values obtained from our PPMM direct power determination and subject weights.

Figures 8A, 8B:
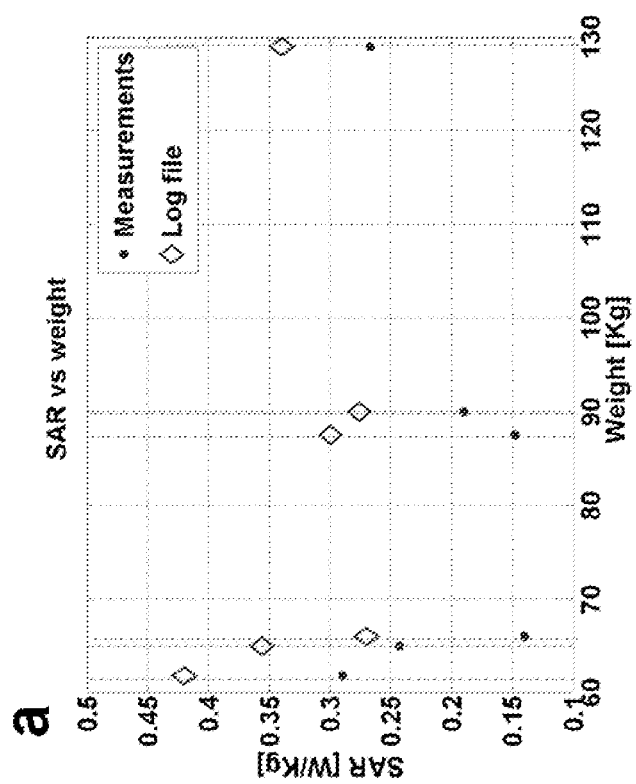
FIGS. 8A-8B show measured SAR for 6 volunteers on the Siemens Medical System's 3 T system (solid dots) compared to scanner reported values from (8A) the log file and (8B) the scanner console.

FIG. 8 shows the calculated SAR values from the real-time power monitor versus the scanner reported values for 3 T Siemens scanner. The power delivered at the output of the Q-hybrid is 90±2% of the power measured at the RF amplifier output. SAR values listed in the Siemens log file differ from those reported at the console: Siemens does not state which values they use. In any case, as with the Philips scanner, the Siemens scanner overestimated SAR. The Siemens scanner log overestimated SAR by up to 103% while the console values were up to 71% above the actual measured SAR.

Discussion

Some embodiments of the current invention address the problem of providing accurate real-time measurements of the RF power delivered to the body, which is inadequately served by existing technology. Specifically, we found that two commonly available commercial RF power meters are unsuitable for the full range of DRs, duty cycles and pulse types encountered in MRI. This was further underscored by differences and errors in power monitoring for short and long RF pulses in the Philips scanner. We therefore developed a real-time, multi-channel power monitoring system according to an embodiment of the current invention that is suitable for a full range of MRI RF pulses and sequences operating over a frequency range that will accommodate scanners with fields up to 10 T.[34]

The accuracy of measurements provided by our power monitoring system was independently validated three ways: 1) on the bench using the Ladybug power meter (FIG. 4); 2) using the 3 T scanner's power monitoring unit at the output of the amplifier for high-power, short RF pulses (FIG. 7A); and 3) by measuring the losses in the 3 T scanner's RF chain using our power monitor and comparing the results with independent measurements made with a network analyzer.

Our new power monitoring system was used to determine the true power deposited and the body-average SAR delivered to adult volunteers in two clinical 3 T MRI systems. The results showed that the scanners almost always overestimate the body-average SAR as compared to the actual power deposited. The overestimates were as much as 120% and 100%, respectively, in the Philips and Siemens 3 T systems studied here (FIG. 7C, 7D; FIG. 8). Unfortunately, the exact details of the manufacturer's SAR modeling are proprietary, precluding the identification of specific causes for the differences. Nevertheless, the data in FIG. 7 suggest Philips' use of a worst-case estimate that is independent of the subject loading, while Siemens' model evidently depends on the subject's weight (FIG. 8). Although the evaluations were performed on the scanner's whole-body coils with sample-dominant losses, application of the power monitoring system is not limited by coil geometry, and similar measurements could be performed on other vendors' scanners and other coil sets, including multi-transmit systems at various field strengths.[34]

The power monitoring system and protocol presented here provide measures of the total power deposited in the body during MRI, or the body average SAR defined as the total power divided by the subject's weight.[1, 2] Local SAR exposure, such as peak 1-g or 10-g averages, are also important for safety compliance.[1,2] At present, these must be obtained by numerical electromagnetic modeling,[11-14, 35-37] from which ratios of the peak local SAR to the total power can be derived. These are, however, anatomy dependent. In practice, the total deposited power may be used in conjunction with numerical electromagnetic models to provide estimated local SAR values.[17, 35-40]

In the Philips scanner, because of losses in the cables, RF coil and other transmit chain components, the power reaching the imaging subject in the Philips scanner was less than half the power supplied by the RF transmitter. The smaller power loss for the Siemens scanner indicates the use of lower loss components. Moreover, both scanners' whole-body SAR estimates reported to the scanner operator seem conservatively overstated. While this may provide an extra safety margin for RF exposure, it nevertheless means that scanner SAR values are not reliable for specifying RF exposure when testing the MRI safety of peripheral, implanted and interventional devices.[3, 20] The overestimate may also limit high-SAR pulse sequences, forcing unnecessary reductions in duty cycle or pulse power that increase scan time and/or compromise efficiency.

Some embodiments of the current invention can provide a versatile approach to accurately measure, in real-time, the total RF power deposition during MRI, independent of the scanner. We have used our real-time power monitoring system to demonstrate deficiencies in commercial scanner reported RF SAR values in some examples. Some embodiments can be used to monitor regulatory compliance, SAR dosimetry, evaluation of scanner function following burn injuries and for setting RF exposure levels during device safety testing. In addition, applications of the current invention are not limited to MRI, but can be used for measuring RF power in other applications including radar, medical RF diathermy, RF ablation systems, and RF telecommunications systems.

REFERENCES

1. Guidance for Industry and FDA: "Staff Criteria for Significant Risk Investigations of Magnetic Resonance Diagnostic Devices," United States Food and Drug Administration (FDA), 2003.
2. Medical electrical equipment—Part 2-33: "Particular requirements for the safety of magnetic resonance equipment for medical diagnosis," European Committee for Electrotechnical Standardization Central Secretariat, IEC Report No. 60601-2-33:2002.
3. P. A. Bottomley, A. Kumar, W. A. Edelstein, J. M. Allen and P. V. Karmarkar, "Designing passive MRI-safe implantable conducting leads with electrodes," Med Phys 37, 3828-3843 (2010).
4. E. Mattei, G. Calcagnini, M. Triventi, F. Censi, P. Bartolini, W. Kainz and H. Bassen, "MRI induced heating of pacemaker leads: effect of temperature probe positioning and pacemaker placement on lead tip heating and local SAR," Conf Proc IEEE Eng Med Biol Soc 1, 1889-1892 (2006).
5. H. Muranaka, T. Horiguchi, S. Usui, Y. Ueda, O. Nakamura and F. Ikeda, "Dependence of RF heating on SAR and implant position in a 1.5 T MR system," Magn Reson Med Sci 6, 199-209 (2007).
6. W. R. Nitz, G. Brinker, D. Diehl and G. Frese, "Specific absorption rate as a poor indicator of magnetic resonance-related implant heating," Invest Radiol 40, 773-776 (2005).
7. P. A. Bottomley and E. R. Andrew, "RF magnetic field penetration, phase-shift and power dissipation in biological tissue: implications for NMR Imaging," Physics in Medicine and Biology 23, 630-643 (1978).
8. P. A. Bottomley, R. W. Redington, W. A. Edelstein and J. F. Schenck, "Estimating radiofrequency power deposition in body NMR imaging," Magn Reson Med 2, 336-349 (1985).
9. P. A. Bottomley and W. A. Edelstein, "Power deposition in whole-body NMR imaging," Med Phys 8, 510-512 (1981).
10. C. Wang, G. X. Shen, J. Yuan, P. Qu and B. Wu, "Theoretical and experimental investigation of the relationship among SAR, tissues and radio frequencies in MRI," Physica Medica 21, 61-64 (2005).
11. C. M. Collins and Z. Wang, "Calculation of radiofrequency electromagnetic fields and their effects in MRI of human subjects," Magn Reson Med 65, 1470-1482 (2011).
12. H. Homann, P. Bornert, H. Eggers, K. Nehrke, O. Dössel and I. Graesslin, "Toward individualized SAR models and in vivo validation," Magn Reson Med 66, 1767-1776 (2011).
13. Z. Wang, J. C. Lin, W. Mao, W. Liu, M. B. Smith and C. M. Collins, "SAR and temperature: simulations and comparison to regulatory limits for MRI," J Magn Reson Imaging 26, 437-441 (2007).
14. S. Oh, A. G. Webb, T. Neuberger, B. Park and C. M. Collins, "Experimental and numerical assessment of MRI-induced temperature change and SAR distributions in phantoms and in vivo," Magn Reson Med 63, 218-223 (2010).
15. P. Ehses, F. Fidler, P. Nordbeck, E. D. Pracht, M. Warmuth, P. M. Jakob and W. R. Bauer, "MRI thermometry: Fast mapping of RF-induced heating along conductive wires," Magn Reson Med 60, 457-461 (2008).
16. "U.S Food and Drug Administration, Center for Devices and Radiological Health, MAUDE data base reports of adverse events involving medical devices. (http://www.accessdata.fda.gov/scripts/cdrh/cfdocs/cfMAUDE/TextSearch.cfm). Simple search with search term: magnetic resonance, then screen individual entries for RF burn injuries."
17. J. P. Stralka and P. A. Bottomley, "A prototype RF dosimeter for independent measurement of the average specific absorption rate (SAR) during MRI," J Magn Reson Imaging 26, 1296-1302 (2007).
18. F. G. Shellock, "Comments on MR heating tests of critical implants," J Magn Reson Imaging 26, 1182-1185 (2007).
19. A. M. El-Sharkawy, D. Qian and P. A. Bottomley, "The performance of interventional loopless MRI antennae at higher magnetic field strengths," Med Phys 35, 1995-2006 (2008).
20. K. B. Baker, J. A. Tkach, J. A. Nyenhuis, M. Phillips, F. G. Shellock, J. Gonzalez-Martinez and A. R. Rezai, "Evaluation of specific absorption rate as a dosimeter of MRI-related implant heating," J Magn Reson Imaging 20, 315-320 (2004).
21. G. Brix, M. Reinl and G. Brinker, "Sampling and evaluation of specific absorption rates during patient examinations performed on 1.5-Tesla MR systems," Magn Reson Imaging 19, 769-779 (2001).
22. P. A. Bottomley, "Turning up the heat on MRI," Journal of the American College of Radiology 5, 853-855 (2008).
23. W. A. Edelstein, G. H. Glover, C. J. Hardy and R. W. Redington, "The intrinsic signal-to-noise ratio in NMR imaging," Magn Reson Med 3, 604-618 (1986).
24. A. Kumar, W. A. Edelstein and P. A. Bottomley, "Noise figure limits for circular loop MR coils," Magn Reson Med 61, 1201-1209 (2009).
25. A. El-Sharkawy, D. Qian, A. Bottomley and W. Edelstein, "A Multi-Channel, High Dynamic Range, Real Time RF Power Deposition Monitor", Proc Int Soc Magn Reson Med p. 496. Montreal, Canada, (2011).
26. W. Edelstein, "Radiofrequency Systems and Coils for MRI and MRS," Encyclopedia of Magnetic Resonance. (2007).
27. A. El-Sharkawy, D. Qian, A. Bottomley and W. Edelstein, "Accurate Measurement of RF Power Deposition During 3 T MRI", 18th Annual Meeting, Int Soc Magn Reson Med p. 3853. Stockholm, Sweden, (2010).
28. L. Zaremba, "FDA Guidelines for Magnetic Resonance Equipment Safety", The American Association of Physicists in Medicine Annual Meeting, p. 8356. Palais des Congrès de Montréal, (2002).
29. T. S. Ibrahim, A. M. Abduljalil, B. A. Baertlein, R. Lee and P. M. L. Robitaille, "Analysis of B1 field profiles and SAR values for multi-strut transverse electromagnetic RF coils in high field MRI applications," Physics in Medicine and Biology 46, 2545-2555 (2001).
30. W. A. Edelstein, O. M. Mueller, R. Frey and D. Vatis, "Electronic method for eliminating prescanning RF transmitter amplitude adjustment", Society of Magnetic Resonance in Medicine Sixth Annual Meeting, p. 372. New York, N.Y., USA, (1987).
31. T. S. Ibrahim, R. Lee, A. M. Abduljalil, B. A. Baertlein and P. M. Robitaille, "Dielectric resonances and B(1) field inhomogeneity in UHFMRI: computational analysis and experimental findings," Magn Reson Imaging 19, 219-226 (2001).
32. S. Akoka, F. Franconi, F. Seguin and A. Le Pape, "Radiofrequency map of an NMR coil by imaging," Magn Reson Imaging 11, 437-441 (1993).
33. M. Schar, E. J. Vonken and M. Stuber, "Simultaneous B(0)- and B(1)+-map acquisition for fast localized shim, frequency, and RF power determination in the heart at 3 T," Magn Reson Med 63, 419-426 (2010).
34. E. Weber, B. K. Li, F. Liu and S. Crozier, "A ultra high field multi-element transceive volume array for small animal MRI," Conf Proc IEEE Eng Med Biol Soc 2008, 2039-2042 (2008).
35. P. A. Bottomley and P. B. Roemer, "Homogeneous tissue model estimates of RF power deposition in human NMR studies—local elevations predicted in surface coil decoupling," Ann. N.Y. Acad. Sci. 649, 144-159 (1992).
36. D. Simunic, "Calculation of energy absorption in a human body model in a homogeneous pulsed high-frequency field," Bioenerg. Bioenerg. 47, 221-230 (1998).
37. W. Liu, C. M. Collins and M. B. Smith, "Calculations of B-1 distribution, specific energy absorption rate, and intrinsic signal-to-noise ratio for a body-size birdcage coil loaded with different human subjects at 64 and 128 MHz," Appl. Magn. Reson. 29, 5-18 (2005).
38. C. M. Collins, S. Li and M. B. Smith, "SAR and B1 field distributions in a heterogeneous human head model within a birdcage coil. Specific energy absorption rate," Magn Reson Med 40, 847-856 (1998).
39. C. M. Collins, W. Liu, J. Wang, R. Gruetter, J. T. Vaughan, K. Ugurbil and M. B. Smith, "Temperature and SAR calculations for a human head within volume and surface coils at 64 and 300 MHz," J Magn Reson Imaging 19, 650-656 (2004).
40. U. D. Nguyen, J. S. Brown, I. A. Chang, J. Krycia and M. S. Mirotznik, "Numerical evaluation of heating of the human head due to magnetic resonance imaging," IEEE Trans Biomed Eng 51, 1301-1309 (2004).

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A device with at least one channel for measuring radio frequency (RF) power levels, comprising:
    a power sensor circuit comprising at least one logarithmic amplifier for measuring RF power levels over a high dynamic range and full range of duty cycles used for magnetic resonance imaging (MRI);
    at least one directional RF coupler electrically connected to said at least one power sensor circuit;
    at least one RF attenuator electrically connected to said at least one directional RF coupler; and
    at least one sampling circuit electrically connected to said at least one RF attenuator and said at least one directional RF coupler,
    wherein said at least one sampling circuit performs analog-to-digital conversion of electrical signals received to provide digitals signals for measuring the RF power level in the at least one channel, and
    wherein said at least one RF attenuator is configured to receive an RF signal from said at least one directional RF coupler and provide a signal to said power sensor circuit.

2. The device of claim 1, further comprising a computer configured to communicate with said at least one sampling circuit to receive said digital signals.

3. The device of claim 2, further comprising a display configured to communicate with said computer, wherein said computer is further configured to calculate measured peak power from said digital signals from said at least one channel in real time, and said display is configured to communicate with said computer to provide real-time display of said measured peak power.

4. The device of claim 3, wherein said computer is further configured to calculate measured average power from said digital signals in real time from said at least one channel, and said display is configured to communicate with said computer to provide real-time display of said measured average power from said at least one channel.

5. The device of claim 1, wherein the at least one channel is more than one channel, wherein each channel comprises a power sensor circuit comprising a logarithmic amplifier connected to a directional RF coupler electrically connected to a RF attenuator electrically connected to at least one sampling circuit, and
    wherein each said sampling circuit is electrically also connected to each RF attenuator to provide multichannel RF measurements.

6. The device of claim 5, wherein the at least one channel is four channels.

7. The device of claim 1, wherein said high dynamic range, low duty cycle RF power levels are produced by a magnetic resonance imaging (MRI) system and said device is MRI compatible.

8. The device of claim 7, wherein said device is adapted for monitoring RF exposure of a subject in said MRI system,
    wherein said MRI system operates in a frequency range of 1 MHz to 400 MHz.

9. The device of claim 8, further comprising a Q-hybrid transducer.

10. A method of monitoring radio frequency (RF) exposure proximate an RF emitting device, comprising connecting an RF monitoring system according to claim 1 to an RF power source of said RF emitting device.

11. The method of claim 10, wherein said RF emitting device is a magnetic resonance imaging (MRI) system.

12. The method of claim 10, wherein said RF power source is an RF coil of an MRI system.

13. The method of claim 10, wherein said RF emitting device is at least one of a radar system or a telecommunications system, or a medical RF diathermy system, or a RF ablation system.

14. The device of claim 1, wherein the at least one channel is a plurality of channels.

15. The device of claim 14, wherein the at least one channel is six channels.

16. The device of claim 1, wherein the high dynamic range is at least 40 dB.

17. The device of claim 1, wherein the high dynamic range is at least 70 dB.

* * * * *